United States Patent [19]

Sailor et al.

[11] Patent Number: 5,453,624
[45] Date of Patent: Sep. 26, 1995

[54] DEVICE FOR DETECTION OF ORGANIC SOLVENTS BY SILICON PHOTOLUMINESCENCE

[75] Inventors: Michael J. Sailor, La Jolle; Vincent V. Doan, San Diego, both of Calif.

[73] Assignee: The Regents of the University of California, Alameda, Calif.

[21] Appl. No.: 267,425

[22] Filed: Jun. 28, 1994

Related U.S. Application Data

[62] Division of Ser. No. 901,753, Jun. 22, 1992, Pat. No. 5,338,415.

[51] Int. Cl.⁶ .............................. F21V 33/00; G01J 1/58
[52] U.S. Cl. ................... 250/458.1; 250/461.1; 250/483.1; 204/129.3
[58] Field of Search ................. 204/129.3, 224 M, 204/129.1, 129.55, 129.75; 250/458.1, 459.1, 461.1, 483.1

[56] References Cited

U.S. PATENT DOCUMENTS

| | | | |
|---|---|---|---|
| 4,409,075 | 10/1983 | Kolbesen | 204/224 M X |
| 4,415,414 | 11/1983 | Burton et al. | 204/129.3 |
| 4,800,282 | 1/1989 | Nishimura | 250/458.1 X |
| 4,874,484 | 10/1989 | Foell et al. | 204/129.75 X |
| 5,030,009 | 7/1991 | Ando et al. | 250/458.1 X |

*Primary Examiner*—Donald R. Valentine
*Attorney, Agent, or Firm*—Brown, Martin, Haller & McClain

[57] ABSTRACT

An n-type silicon (Si) wafer is galvanostatically etched in a hydrofluoric acid (HF)-containing solution while being illuminated with a 300 watt tungsten light source to form porous silicon with luminescent properties. Photoluminescence of the porous silicon is monitored using a short wavelength visible or ultraviolet light source and a monochromator/CCD detector assembly. Upon exposure to organic solvents, the photoluminescence is quenched. Within seconds of removal of the solvent, the original intensity is recovered and further exposure of the porous silicon to organic solvents will again result in quenching of the luminescence.

12 Claims, 1 Drawing Sheet

DEVICE FOR DETECTION OF ORGANIC SOLVENTS BY SILICON PHOTOLUMINESCENCE

This is a divisional of application Ser. No. 07/901,753, filed Jun. 22, 1992 now U.S. Pat. No. 5,338,415.

BACKGROUND OF THE INVENTION

Silicon is known for its ready availability and relative ease in processing for fabrication of electronic devices. It has recently been discovered that by electrochemically and chemically etching single-crystal silicon, nanometer structures are formed which convert the silicon into a highly luminescent material. The "quantum wires" that are formed during the etch photoluminesce in the visible region of the electromagnetic spectrum when illuminated as a result of the increase in effective band gap energy.

While the ability to fabricate photoluminescent silicon has clear implications in the development of optical electronics, other applications are also worthy of exploration.

Many industries, including the electronics industry, utilize a variety of organic solvents and gases which present environmental and/or safety hazards. These solvents can be highly volatile and flammable, and can be toxic and/or carcinogenic to those who are exposed to even relatively low levels of the solvent. Thus, in applications where no alternatives exist for these solvents, it is necessary to provide means for determining whether organic solvents are present in areas which should be free of such hazardous chemicals.

SUMMARY OF THE INVENTION

It is an object of the present invention to provide a device for detecting the presence of organic solvent molecules.

It is another object of the present invention to provide a means for continuously monitoring the presence of organic solvent molecules, where the device is capable of repeated detections.

Still another object of the present invention is to provide a device which is capable of detecting dipolar gases.

In an exemplary embodiment, an n-type silicon (Si) wafer is galvanostatically etched in a hydrofluoric acid (HF)-containing solution while being illuminated with a 300 watt tungsten light source to form porous silicon with luminescent properties. The wafer is rinsed with ethanol and dried under a stream of nitrogen gas.

Photoluminescence of the porous silicon is monitored using a short wavelength visible or ultraviolet light source and a monochromator/CCD detector assembly. Upon exposure to organic solvents, in either liquid or vapor form, the photoluminescence is quenched. Immediately after exposure to the solvent, the emission maximum intensity is significantly decreased, and the corresponding emission maximum wavelength shifts to a shorter wavelength. Within seconds of removal of the solvent, the original intensity is recovered and further exposure of the porous silicon to organic solvents will again result in quenching of the luminescence.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF THE PREFERRED EMBODIMENT

Figure 1:
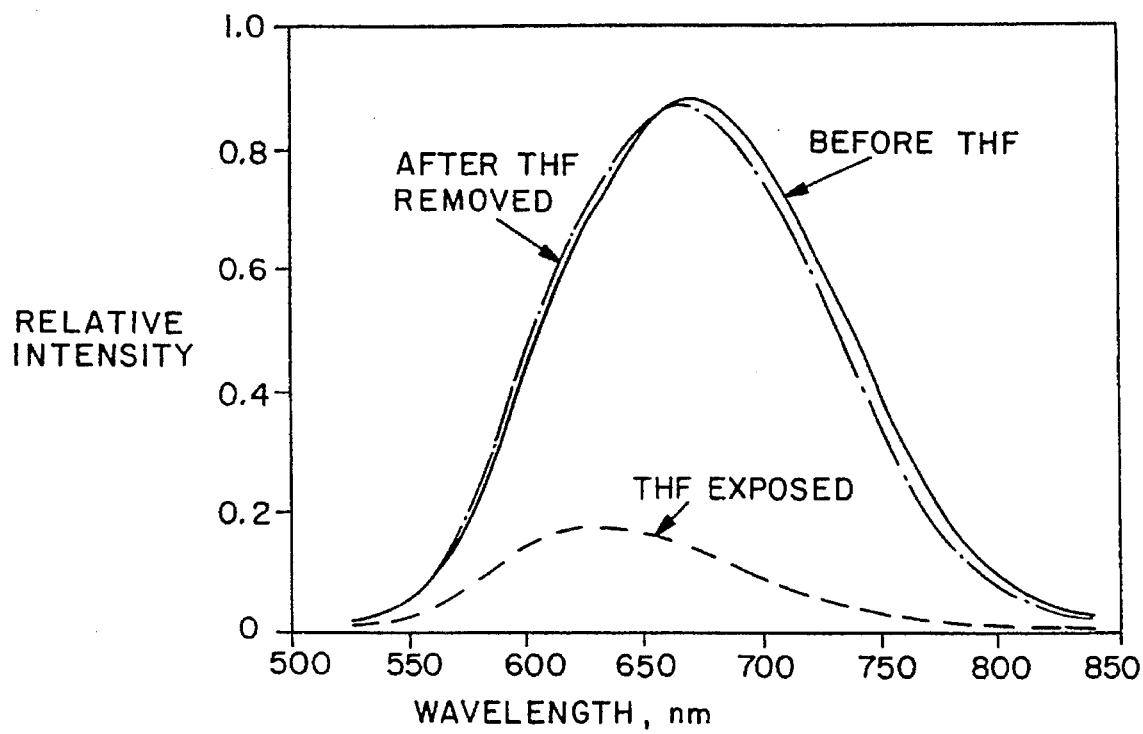
FIG. 1 is a plot of wavelength versus relative intensity of photoluminescence before, during and after exposure of porous silicon to a solvent.

An n-type silicon wafer (0.642 ohm-cm resistivity, (100) orientation) is submersed in a solution of 50:50 ethanol/HF after attaching an electrode to the backside of the wafer. A second electrode is immersed in the bath, and a current is applied to the electrodes such that a low current density is initiated within the solution. The wafer is illuminated with a 300 watt tungsten lamp during etch for approximately 30 minutes at 5 mA/cm$^2$, followed by a 25 second etch at 50 mA/cm$^2$. The wafer is rinsed with ethanol and dried under a stream of nitrogen.

The etch time is not critical, however, resolution improves with longer etch times. The etch time will also impact interference behavior when the porous silicon is excited with white light. In .this case, the longer the etch, the longer the wavelength of the false color generated by the interference. The current density need not be exactly 5 mA/cm$^2$, but will be most effective if kept within a factor of 10 of 5 mA/cm$^2$.

The material which is used for formation of porous Si is not limited to single-crystal n-type silicon. P-type silicon wafers can also be used, the resistivity ranges for both p- and n-type running from near intrinsic to just below levels where metallic properties are encountered. Some workers have attained photoluminescence in amorphous silicon, and silicon on sapphire (SOS) or other insulating substrates may also be used.

Exposure wavelengths during electrochemical etch can be derived from any kind of light source. In bulk conversion of silicon to a porous condition, such as may be used for general use detectors of the present invention, longer wavelengths, in the red regions, may be desired for deeper penetration of the etch into the silicon. For better resolution, shorter wavelengths (green, blue, UV) may be desirable.

For practical applications as an environmental monitor, the porous silicon detector is placed in air and monitored using a short visible wavelength or ultraviolet excitation source with a monochromator/CCD detector assembly. For evaluation purposes in laboratory testing, the silicon wafers were placed in a light-transmissive vacuum chamber which was evacuated to 50 mTorr and back-filled with nitrogen three times before analysis. Wafers for vapor analysis were left under vacuum and wafers which were to be directly subjected to neat (liquid) solvent were handled under purified nitrogen, and exposed to the solvent using conventional vacuum line or Schlenk and syringe techniques, as are known in the art. All solvents were purified and deoxygenated according to published procedures (see, e.g., Shriver, D. F., et al., *The Manipulation of Air-Sensitive Compounds*, John Wiley & Sons, New York, 1986, pp. 84–92), and the solvents used in vapor exposure studies were freeze-pump-thaw degassed three times prior to use. The photoluminescence of the porous silicon samples was monitored using a 442 nm He/Cd laser excitation source and a ¼ m monochromator/CCD detector setup. The porous silicon photoluminesces to emit light in the 500 nm to 800 nm wavelength range. The amount of luminescence quenching by each solvent was determined as the relative luminescence intensity directly before and one minute after exposure to the solvent ($I/I_0$).

The emission spectra of a luminescent porous silicon layer before and after exposure to approximately 160 torr of tetrahydrofuran (THF) is illustrated in FIG. 1. Immediately after exposure to the solvent, the emission maximum intensity at 670 nm decreased by a factor of four, and the emission maximum shifted to 630 nm. The emission spectrum recovered to the original intensity within seconds of evacuation of the excess solvent vapor, although the emission maximum at this point has shifted slightly to approximately 660 nm. Repeated THF exposure/evacuation cycles reproduced the latter two spectra. Exposure to gaseous diethyl ether, methylene chloride, toluene, o-xylene, ethanol, and methanol also resulted in reversible quenching.

Figure 2:
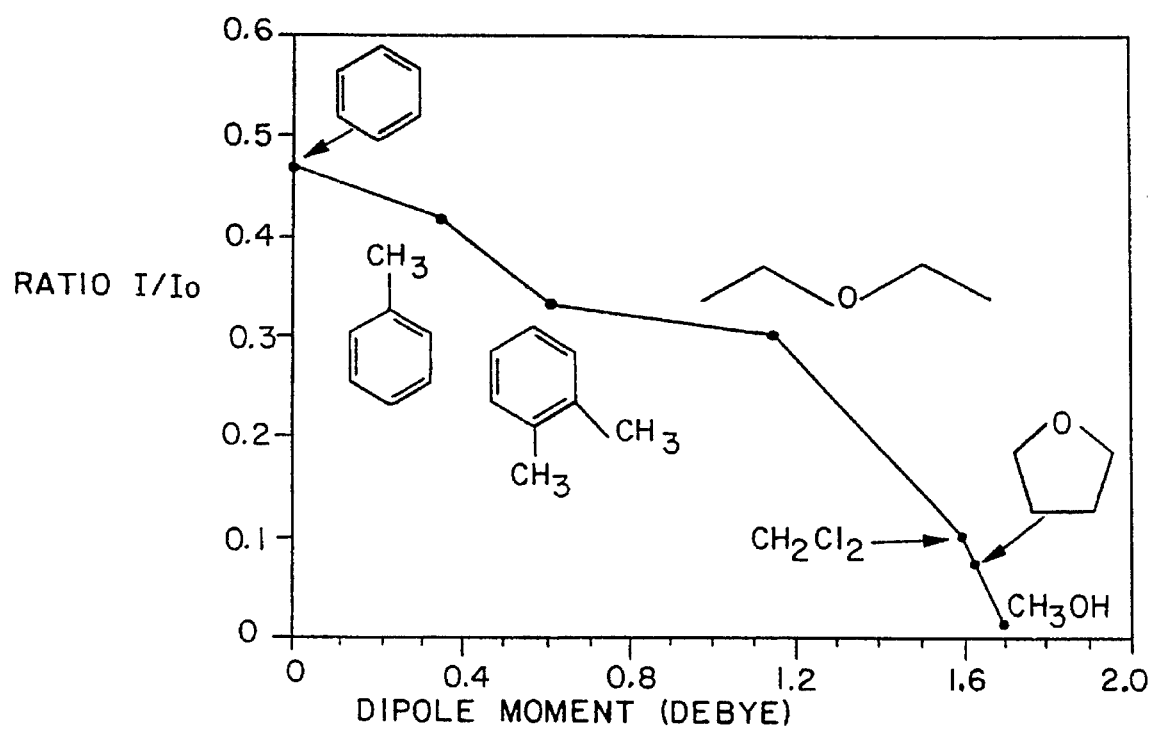
FIG. 2 is a plot of dipole moment versus ratio of luminescence intensity before and after exposure to a solvent.

The correlation of luminescence quenching ratios ($I/I_0$) of the neat solvents to the dipole moments of the gas phase solvents is illustrated in FIG. 2. The relative intensity tracks with the dipole moment of the gases, however, the mechanism of emission quenching is not known. All solvents that were investigated reduced the emission intensity of porous silicon, indicating that the solvent interactions reduce carrier trapping in silicon. Addition of a toluene solution of the non-polar electron donor ferrocene to a porous silicon wafer immersed in toluene results in a complete loss of luminescence, suggesting that quenching by interfacial electron transfer can also occur.

The correlation between quenching and dipole moment suggests the possibility of using porous silicon detectors for detecting the presence of chemicals or detecting other gaseous materials, or for detecting the presence of chemicals or forces which will affect, interact with or modify the dipole moments of the gaseous molecules.

Generally, the extreme sensitivity of the luminescent porous silicon surface makes it well suited for applications as chemical sensors. A detector assembly based on porous silicon can be made compact by using a solid state laser as an excitation source, or the excitation source may be provided by way of optical fibers.

It will be evident that there are additional embodiments which are not illustrated above but which are clearly within the scope and spirit of the present invention. The above description and drawings are therefore intended to be exemplary only and the scope of the invention is to be limited solely by the appended claims.

We claim:

1. A device for detection of an organic solvent comprising:
   a silicon surface disposed on a substrate wherein said silicon surface has been electrochemically etched in a solution containing hydrofluoric acid while said silicon surface is exposed to high intensity light to form micro-pores in said silicon surface;
   a light source for illuminating said silicon surface, said light source emitting light at a wavelength at which said silicon surface photoluminesces;
   a detector for detecting photoluminscence from said silicon surface;
   wherein said detector detects said photoluminescence from said silicon surface at a first level when said silicon surface is exposed to said light from said light source and said detector detects said photoluminescence at a second level when said photoluminescence is diminished by exposure to said organic solvent, said photoluminescence returning substantially to said first level when said organic solvent is removed.

2. A device as in claim 1 wherein said silicon surface comprises a face of a silicon wafer.

3. A device as in claim 2 wherein said silicon wafer comprises single-crystal silicon.

4. A device as in claim 2 wherein said silicon wafer is n-type silicon.

5. A device as in claim 2 wherein said silicon wafer is p-type silicon.

6. A device as in claim 1 wherein said silicon surface comprises at least one layer of silicon on an insulating substrate.

7. A device as in claim 1 wherein said high intensity light is from a tungsten lamp.

8. A device as in claim 1 wherein said wavelength of said light source for illuminating said silicon surface is within a range of short visible to ultraviolet wavelengths.

9. A device as in claim 8 wherein said light source is a helium/cadmium laser and said wavelength is 442 nm.

10. A device as in claim 1 wherein said detector is a monochromator/CCD detector.

11. An environmental monitoring device for detection of an organic solvent in an environment, the device comprising:
    a light source for emitting light within a wavelength range of short visible to ultraviolet light;
    a porous silicon detector disposed in a light path of said light source, wherein said porous silicon detector photoluminesces when illuminated by said light; and
    an optical detector for detecting photoluminescence from said porous silicon detector;
    wherein said porous silicon detector photoluminesces at a first level when exposed to said light and said photoluminescence is diminished to a second level in response to said organic solvent in the environment and returns substantially to said first level when said organic solvent is removed from the environment.

12. An environmental monitoring device as in claim 11 wherein said porous silicon detector comprises a silicon surface which is electrochemically etched in a solution containing hydrofluoric acid while said silicon surface is exposed to a high intensity light to form micro-pores in said silicon surface.

* * * * *